United States Patent [19]

Eymond

[11] 4,112,226

[45] Sep. 5, 1978

[54] PROCESS FOR REMOVING NON-FLUORESCENT TRIAZINE DERIVATIVE IMPURITIES FROM FLUORESCENT AGENTS

[75] Inventor: Philip Richard Norman Eymond, Wirral, England

[73] Assignee: Lever Brothers Company, New York, N.Y.

[21] Appl. No.: 734,686

[22] Filed: Oct. 22, 1976

[30] Foreign Application Priority Data

Oct. 24, 1975 [GB] United Kingdom ............... 43849/75

[51] Int. Cl.$^2$ ............................................ C07D 251/08
[52] U.S. Cl. ..................... 542/461; 260/701; 260/704; 544/113; 544/194; 544/204
[58] Field of Search .................... 260/240 B; 542/461, 542/460

[56] References Cited

U.S. PATENT DOCUMENTS

| 2,612,501 | 9/1952 | Wilson ....................... 260/240 B UX |
| 2,703,801 | 3/1955 | Rottschaefer et al. ... 260/240 B UX |
| 3,511,833 | 5/1970 | Tscharner ....................... 260/240 B |
| 3,741,903 | 6/1973 | Evans ........................... 260/240 B X |
| 3,951,960 | 4/1976 | Heath et al. ....................... 260/240 B |
| 3,956,283 | 5/1976 | Fleck ............................... 260/240 B |

*Primary Examiner*—Floyd D. Higel

*Attorney, Agent, or Firm*—Kenneth F. Dusyn; James J. Farrell; Melvin H. Kurtz

[57] ABSTRACT

A method for removing non-fluorescent triazine derivative impurities having the structural formula:

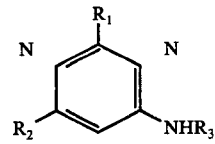

wherein $R_1$ is a hydroxy group or a halogen atom, $R_2$ is a hydroxy group or the group —$NR_4R_5$, each of $R_4$ and $R_5$ being a hydrogen atom, alkyl, substituted alkyl, aryl or substituted aryl group, or $R_4$ or $R_5$ being combined in a heterocyclic ring, and $R_3$ is an alkyl, substituted alkyl, aryl or substituted aryl group, from fluorescent agents belonging to the class of compounds of 4,4'-di(sym-triazinylamino) stilbene-2,2'-disulphonic acids and salts thereof, by washing said fluorescent agent with a dilute aqueous solution of an alkali metal hydroxide under atmospheric pressure and at a temperature not exceeding 75° C.

6 Claims, No Drawings

PROCESS FOR REMOVING NON-FLUORESCENT TRIAZINE DERIVATIVE IMPURITIES FROM FLUORESCENT AGENTS

This invention relates to a process for the purification of fluorescent agents. More particularly the invention relates to a method for removing triazine derivatives having the structural formula:

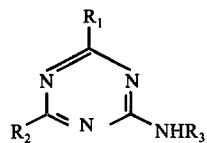

wherein
$R_1$ is a hydroxy group or a halogen atom,
$R_2$ is a hydroxy group or the group $-NR_4R_5$, each of $R_4$ and $R_5$ being a hydrogen atom, or an alkyl, substituted alkyl, aryl or substituted aryl group, or $R_4$ and $R_5$ being combined in a heterocyclic ring, and $R_3$ is an alkyl, substituted alkyl, aryl, or substituted aryl group,
from fluorescent agents belonging to the group of derivatives of 4,4'-di(sym-triazinylamino)stilbene-2,2'-disulphonic acid and the salts thereof.

Commercial fluorescent agents of this group generally contain various levels of triazine derivatives of formula (I) above as impurities, which are apparently formed during the preparation of the fluorescent agents. These impurities, if present in too high a concentration in the fluorescent agent, render the unpurified fluorescent agent unsatisfactory for use in bleaching detergent compositions comprising an organic peracid, or an inorganic percompound, such as sodium perborate, and an organic peracid precursor, e.g. N,N,N',N'-tetraacetylethylene diamine, as it would cause discolouration and the generation of foul odours in the composition during storage.

A method for the purification of fluorescent agents from the group of derivatives of 4,4'-di(sym-triazinylamino) stilbene-2,2'-disulphonic acid and salts thereof, hereinafter termed as DTASDS-fluorescent agents is disclosed in British Patent Specification No. 1,286,459. The method uses boiling water to which a minimum amount of ethanol is added to dissolve the substance. The solution thus formed is cooled to about 60°–65° C, whereupon less soluble impurities in the fluorescent agent are precipitated and are removed from the solution by filtration. The filtrate is then cooled to room temperature to precipitate the fluorescent agent which is itself removed by filtration and subsequently dried. Although a satisfactory pure product can be obtained with this method, it is quite a roundabout way of working, making the process unsuitable for large scale operation.

Another process for upgrading a bis-triazinylamino stilbene derivative is described in British Patent Specification No. 997,044, comprising a heat-pressure treatment in a closed vessel in the presence of an alkaline material in aqueous medium, by which the compound is transformed from the α-crystalline form to the β-crystalline form.

It is an object of the present invention to provide an improved method for the purification of DTASDS-fluorescent agents by a simple extraction technique without the above disadvantages.

It has now been found unexpectedly and surprisingly that triazine derivative impurities of formula (I) above can be satisfactorily removed from DTASDS-fluorescent agents by contacting said fluorescent agents at atmospheric pressure and at relatively low temperature with an aqueous medium comprising a strong base.

The strong bases which can be employed in the practice of this process are the alkali metal hydroxides, though strong organic bases may be used as well. Preferred bases are the alkali metal hydroxides, sodium hydroxide and potassium hydroxide being particularly preferred.

The above bases are used as a dilute aqueous solution, generally at a concentration of about 0.5–5%. Higher concentrations may be used but are in general of no further benefit and hence unnecessary. A preferable concentration range is 1–4%.

The process of the invention can be conveniently carried out at ambient temperatures and at atmospheric pressure, wherein the fluorescent agent is contacted with the strong base in an aqueous medium. The amount of aqueous base solution used is not very critical but is rather a matter of balancing economy and proper processing technique, lying within the general ability of the man skilled in the art when practising the invention.

It will be understood that amounts should be chosen in such a way that they would not give handling difficulties in one way or another. Nevertheless, without limiting the scope of the present invention, it can be said that an amount of about 25–150 milliliters of base solution per gram of active fluorescent agent compound has been found most convenient. A preferable range is from about 25–100 milliliters of aqueous base solution per gram of fluorescent agent compound. Advantageously stirring can be applied to secure good contact between the fluorescent agent and the base. Recovery of the fluorescent agent can be accomplished by filtration, followed by an aqueous wash and drying. Altogether the process of the invention is relatively simple and yet so surprisingly effective that in general a single treatment is quite sufficient to produce a fluorescent agent of such purity that it is immediately suitable for incorporation in a detergent bleach composition without causing malodour and discolouration. Of course, if for some reason a still lower level of triazine impurities is required, the treatment can be repeated, for which conveniently the recovered fluorescent agent before drying can be taken.

A significant advantage of the present process over the known method is that the fluorescent agent remains undissolved during the whole process, thereby resulting in minimum loss of product.

Although the exact mechanism of triazine impurity extraction effected by the base is not known, it is believed that the malodour causing triazine impurities as defined above react with the base to form water-soluble compounds which can be washed away from the crystalline fluorescent agent. Clearly it is not a pH-effect and the effect obtained from the invention is quite surprising, since experiments have shown that sodium carbonate is totally ineffective. The strong bases that are suitable for use in the present invention should therefore be capable of converting the triazine derivatives of formula (I) above, which are normally water-insoluble into water-soluble compounds.

Increasing the temperature of the process to above ambient values may be applied as desirable to speed up the reaction, although care should be taken to remain well below 100° C., in view of the increased solubility of the fluorescent agent with increase of temperature.

Advantageously the temperature of the process should not exceed 75° C. A preferable and convenient temperature range is from about 20° to 60° C.

An electrolyte, such as sodium chloride, may be added in minor amounts, i.e. generally not more than about 1%, to the aqueous medium to prevent the fluorescent agent from getting into a colloidal state, and also to minimise loss of fluorescent agent by dissolution. In those cases where the fluorescent agent itself already contains a fair amount of electrolytes, such a measure can of course be omitted.

The fluorescent agent compounds which may contain triazine impurities and covered by the present invention are well-known and many such materials are available commercially and have been used in detergent compositions.

Specific DTASDS-fluorescent agent compounds which may be mentioned by way of example are:

(a) 4,4-di(2″,4″-dianilinotriazin-6″-ylamino)-stilbene-2,2′-disulphonic acid and its salt, (b) 4,4′-di(2″-anilino-4″-morpholinotriazin-6″-ylamino)-stilbene-2,2′-disulphonic acid and its salts, (c) 4,4′-di(2″-anilino-4″-N-methylethanolaminotriazine-6″-ylamino)-stilbene-2,2′-disulphonic acid and its salts, (d) 4,4′-di(2″-anilino-4″-diethanolaminotriazin-6″-ylamino)-stilbene-2,2′-disulphonic acid and its salts, (e) 4,4′-di(2″-anilino-4″-dimethylaminotriazin-6″-ylamino)-stilbene-2,2′-disulphonic acid and its salts, (f) 4,4′-di(2″-anilino-4″-diethylaminotriazin-6″-ylamino)-stilbene-2,2′-disulphonic acid and its salts, (g) 4,4′-di(2″-anilino-4″-monoethanolaminotriazin-6″-ylamino)-stilbene-2,2′-disulphonic acid and its salts, (h) 4,4′-di(2″-anilino-4″-(1-methyl-2-hydroxy)ethylaminotriazin-6″-ylamino)-stilbene-2,2′-disulphonic acid and its salts, (i) 4,4″-di(2″-methylamino-4″-p-chloroanilinotriazin-6″ylamino)-stilbenzene-2,2′-disulphonic acid and its salts, and (j) 4,4′-di(2″-diethanolamine-4″-sulphanilinotriazin-6″-ylamino)-stilbene-2,2′-disulphonic acid and its salts.

Usually these fluorescent agents are supplied and used in detergent compositions in the form of their alkali metal salts, for example the sodium salts.

The invention will now be illustrated by way of the following non-limitative Example.

EXAMPLE

Four beakers were filled with respectively:
(1) 50 milliliters of an aqueous 2% NaOH solution.
(2) 50 milliliters of a 50/50 mixture of toluene and an aqueous 2% NaOH solution.
(3) 50 milliliters of an aqueous 2% Na₂CO₃ solution.
(4) 50 milliliters of distilled water.

In each of the beakers was added 1 gram of a commercial DTASDS-fluorescent agent sodium 4,4′-di(2″-anilino-4″-morpholinotriazin-6″-ylamino)-stilbene-2,2′-disulphonate. Each mixture was stirred for 30 minutes at 50° C., cooled off to ambient temperature and the fluorescent agent filtered off. Each fluorescent agent on the filter was then washed with an adequate amount of tap-water containing 1% NaCl until free of alkali and then dried at 100° C. under vacuum.

The results of the quantitative analysis for the non-fluorescent triazine derivative impurities are given in the following Table:

| DTASDS-fluorescent agent | Triazine impurity (identified as AAHT*) |
|---|---|
|  | % by weight |
| untreated | 2.67 |
| 1) Treated with NaOH solution | 0.14 |
| 2) Treated with NaOH/toluene solution | 0.20 |
| 3) Treated with Na₂CO₃ solution | 2.60 |
| 4) Treated with distilled water | 2.77 |

*AAHT = Anilino-anilino-hydroxy triazine

The above results show that sodium carbonate and water are ineffective, whereas NaOH according to the invention removes the malodour causing triazine derivative AAHT of formula (I) above quite effectively.

The fluorescent agents mentioned above were each incorporated at a level of 0.6% in a detergent powder comprising sodium perborate and an activator (N,N,N′,N′-tetra acetyl ethylene diamine) to give the following composition:

| sodium alkyl benzene sulphonate | 14.2% |
|---|---|
| sodium toluene sulphonate | 1.0% |
| coconut ethanolamide | 2.0% |
| alkaline sodium silicate | 9.6% |
| sodium carboxymethyl cellulose | 0.5% |
| sodium sulphate | 12.6% |
| sodium tripolyphosphate | 33.5% |
| sodium perborate | 10.0% |
| N,N,N′,N′-tetra acetyl ethylene diamine | 8.0% |
| ethylene diamine tetra acetate (EDTA) | 0.1% |
| fluorescent agent | 0.6% |
| water to | 100.0% |

The powders were stored in closed bottles at 80° C. and the odour and colour were examined after ½ hour. The following was observed:

|  | Colour | Odour |
|---|---|---|
| Powder + untreated fluorescer | Pink | Strong carbylamine |
| Powder + treated fluorescer (1) | none | none |
| Powder + treated fluorescer (2) | none | none |
| Powder + treated fluorescer (3) | pink | strong carbylamine |
| Powder + treated fluorescer (4) | pink | strong carbylamine |

I claim:
1. A process for removing non-fluorescent triazine derivative impurities having the structural formula:

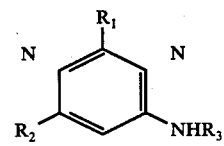

wherein
R₁ is a hydroxy group or a halogen atom,
R₂ is a hydroxy group or the group —NR₄R₅, each of R₄ and R₅ being a hydrogen atom, alkyl, substituted alkyl, aryl or substituted aryl group, and R₃ is an alkyl, substituted alkyl, aryl or substituted aryl group,
from a fluorescent agent of
(a) 4,4-di(2″,4″-dianilinotriazin-6″-ylamino)-stilbene-2,2′-disulphonic acid or its salts,
(b) 4,4′-di(2″-anilino-4″-morpholinotriazin-6″-ylamino)-stilbene-2,2′-disulphonic acid or its salts, (c) 4,4'-di(2''-anilino-4''-N-methylethanolamino-triazin-6''-ylamino)-stilbene-2,2'-disulphonic acid or its salts,
(d) 4,4'-di(2''-anilino-4''-diethanolaminotriazin-6''-ylamino)-stilbene-2,2'-disulphonic acid or its salts,
(e) 4,4'-di(2''-anilino-4''-dimethylaminotriazin-6''-ylamino)-stilbene-2,2'-disulphonic acid or its salts,
(f) 4,4'-di(2''-anilino-4''-diethylaminotriazin-6''-ylamino)-stilbene-2,2'-disulphonic acid or its salts,
(g) 4,4'-di(2''-anilino-4''-monoethanolaminotriazin-6''-ylamino)-stilbene-2,2'-disulphonic acid or its salts,
(h) 4,4'-di(2''-anilino-4''-(1-methyl-2-hydroxy)ethylaminotriazin-6''-ylamino)-stilbene-2,2'-disulphonic acid or its salts,
(i) 4,4''-di(2''-methylamino-4''-p-chloroanilinotrazin-6''-ylamino)-stilbene-2,2'-disulphonic acid or its salts, or
(j) 4,4'-di(2''-diethanolamine-4''-sulphanilinotrazin-6''-ylamino)-stilbene-2,2'-disulphonic acid or its salts, which consists essentially of the steps of contacting said fluorescent agent at atmospheric pressure and at a temperature not exceeding 75° C., with an aqueous solution containing 0.5–5% by weight of an alkali metal hydroxide in an amount of 25–150 milliliters per gram of fluorescent agent, wherein said fluorescent agent remains substantially undissolved, and separating the fluorescent agent from said aqueous solution.

2. Process according to claim 1, wherein said alkali metal hydroxide is sodium hydroxide.

3. The process according to claim 1, wherein the temperature of contact of the fluorescent agent and aqueous solution is between 20° and 60° C.

4. The process according to claim 1, wherein the aqueous solution additionally comprises an electrolyte in an amount of up to 1%.

5. Process according to claim 4, wherein the electrolyte is sodium chloride.

6. The process according to claim 1 wherein said aqueous solution contains 1–4% by weight of an alkali metal hydroxide.

* * * * *